United States Patent [19]

Labinger et al.

[11] Patent Number: 4,707,734
[45] Date of Patent: Nov. 17, 1987

[54] COARSE FLAW DETECTOR FOR PRINTED CIRCUIT BOARD INSPECTION

[75] Inventors: Richard L. Labinger, Trumbull; Natale F. Tinnerino, Redding, both of Conn.; Timothy E. Bryant, Yorba Linda, Calif.

[73] Assignee: The Perkin-Elmer Corporation, Norwalk, Conn.

[21] Appl. No.: 745,967

[22] Filed: Jun. 17, 1985

[51] Int. Cl.[4] ............................................. H04N 7/18
[52] U.S. Cl. .................................. 358/106; 358/101; 382/8
[58] Field of Search ...................... 358/106, 107, 101; 382/8, 25, 48; 364/550, 579, 580; 356/237, 394, 398

[56] References Cited

U.S. PATENT DOCUMENTS

| 4,442,542 | 4/1984 | Lin et al. | 382/8 |
| 4,477,946 | 10/1984 | Linger et al. | 382/8 |
| 4,479,145 | 10/1984 | Azuma et al. | 358/101 X |
| 4,500,202 | 2/1985 | Smyth | 356/237 |
| 4,510,616 | 4/1985 | Lougheed et al. | 382/8 |
| 4,614,430 | 9/1986 | Hara et al. | 382/8 X |

OTHER PUBLICATIONS

"Automatic Copper Pattern Inspection System for PW Boards", Ando et al., Institute of Interconnecting and Packaging Electronic Circuits, WC111-26, May 1984.
"Automatic Inspection for Printed Wiring", Thibadeau et al., Institute for Interconnecting and Packaging Electronic Circuits; Oct. '82.
"Automatic Optical Inspection", Ralph Taylor; Circuits Manufacturing, Feb. '84.
"Automatic Inspection System for PC Boards", Hara et al., CH1755-8, 1982, IEEE.
"Automated Optical Inspection of PC Boards", Bible et al.; Wescon, 1983, Conference Record, vol. 27, Nov. 1983, IEEE.

Primary Examiner—James J. Groody
Assistant Examiner—Victor R. Kostak
Attorney, Agent, or Firm—Thomas P. Murphy; Edwin T. Grimes; Francis L. Masselle

[57] ABSTRACT

A system for detecting flaws in printed circuit boards. The circuit board is scanned by a video camera to provide a serial stream of bits each indicative of a picture element within a particular scan line. The serial stream of bits is formulated into binary numbers each representative of a contiguous path of picture elements composed of $n \times n$ picture elements. Each of these binary numbers are compared with a corresponding one of a set binary numbers stored in memory representative of a perfect master printed circuit board. Failure of the printed circuit board to match the stored master indicates a flaw. The invention also includes means to generate overlapping patches to insure detection of defects which occur in adjacent patches.

13 Claims, 5 Drawing Figures

COARSE FLAW DETECTOR FOR PRINTED CIRCUIT BOARD INSPECTION

BACKGROUND OF THE INVENTION

A printed circuit board comprises a substrate, typically made of fiberglass or mylar whose surface has metal lines formed thereon which are electrical conductors used to connect various circuit components together and/or to external circuitry. In order to keep pace with the integrated circuit industry, feature sizes, i.e., lines and spaces between the metal lines have shrunk to very small dimensions, e.g., 0.005 inches. While techniques for the fabrication of printed circuit boards have greatly advanced in recent years, a certain percentage of printed circuit boards still come out of production with one or more of a variety of flaws. For example, a printed circuit board may have lines and/or spaces too narrow, shorts, opens, pinholes or the like; any one of which may render the board useless. Due to their extremely small sizes visual detection of such flaws in boards with very fine lines is neither technically effective nor economically practical. Thus, automation of the printed circuit board inspection process is an essential requirement in the printed circuit manufacturing business.

The present invention relates to a system for the automatic inspection of printed circuit boards and the like.

BRIEF DESCRIPTION OF THE INVENTION

The present invention relates to an image matching technique of inspection in which the printed circuit board being tested is compared with a stored master to determine acceptability. In doing so patches of the test surface made up of n×n picture elements, i.e., pixels are compared with corresponding patches of the stored master. If there is a mismatch between any pair of corresponding patches, a flaw is indicated.

In carrying out the present invention a video camera, e.g., a CCD array is scanned relative to the illuminated test surface. The CCD array is sensitized at a plurality of locations as it scans along the test surface. Each of these locations is designated a scan line. All the bits attributable to a scan line are transferred out of the CCD array in series. Each of the bits is thus representative of a pixel seen by the CCD array in a particular scan line.

A unique arrangement of delay lines and shift registers convert the serial stream of bits into parallel outputs of n bits each from which other circuitry forms patches of n×n pixels.

Another unique arrangement converts each set of n bits into a binary number and adds the binary number representative of each new set of n bits to the last until a binary number representative of n×n bits referred to as a patch is generated.

Each of these binary numbers is compared with a corresponding binary number obtained from the stored master until the entire printed circuit board is inspected. If one or more test patches fails to match its corresponding reference patch, a flaw is indicated.

By using this patch matching technique, patches of n×n pixels, where n may equal any number, may be used which considerably reduces the amount of memory required to store the master since each patch may be represented by a single binary number stored in memory instead of individual pixels as in the case when inspection is performed on a pixel by pixel basis. If memory size and data rate are not of concern, the image may be stored on a pixel by pixel basis.

A further feature of the present invention provides fifty percent overlapping of the test and master patches in the x, y plane of the printed circuit board to assure full detection of defects which occur in adjacent patches. For example, in the worst case, part of a defect may appear in the corner of four adjacent patches, normally generating only one-fourth the defect signal when no overlap is used. However, by using fifty percent overlapping patches, one hundred percent of this defect signal is detected.

DESCRIPTION

Figure 1:
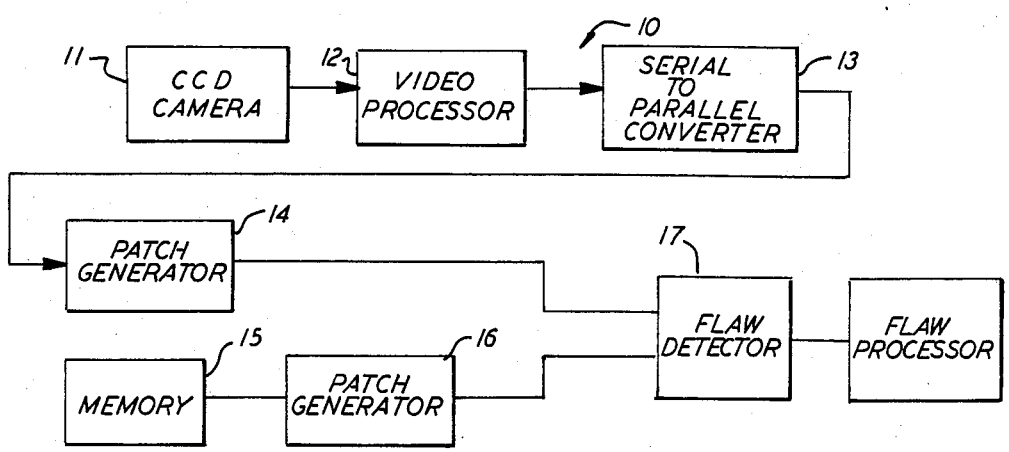
FIG. 1 is a block diagram of the inspection system of the present invention.

Referring now to FIG. 1, there is shown in simplified block diagram form the flaw inspection system 10 of the present invention. A video camera 11 which may be a charged coupled device (CCD) array is made to scan across the length of the surface of the printed circuit board or other surface to be inspected. Depending on the size of the surface to be inspected and the length of the CCD array the surface to be inspected may be scanned in one scanning action or may require more than one scan to view the entire surface to be inspected. A CCD array of the type used in the present invention comprises a plurality of light sensitive elements arranged in a straight line. In a practical embodiment the CCD array is a linear array having 2048 light sensitive elements and is 1.024 inches in length. Under these conditions each light sensitive element in the CCD array is $0.0005 \times 0.0005$ inch square and is capable of resolving over its length 2048 picture elements or pixels each one of which is $0.0005 \times 0.0005$ inch square. CCD arrays could, of course, be used having a greater or smaller number of light sensitive elements in longer or shorter arrays depending on the degree of resolution required and scanning swath desired.

As is well known, a CCD array must be sensitized to view a surface along its array length and then the image information transferred out for processing. To inspect a surface, this sensitization and transfer of data must occur a large number of times. For example, if one wishes to view a surface 1.024 by 1.024 inches at the highest possible resolution then a CCD array having 2048 light sensitive elements each $0.0005 \times 0.005$ inch square would have to be sensitized and emptied 2048 times during the scan. Thus, in this particular example, it takes 2048 scan lines to view the entire surface. Therefore, for each scan line the CCD array outputs an analog signal representative of 2048 pixels. If the surface to be inspected exceeds 1.024 inches in width, more than one scan may be required.

The output of the video camera 11 is connected to video processor 12. The video processor 12 functions as an A to D converter to transform the analog signal representative of the pixels in each scan line to a digital signal comprising serial 0's and 1's each representative of a pixel as viewed by the CCD array in each scan line.

The video processor 12 is connected to serial to parallel converter 13. The serial to parallel converter 13 functions to convert the serial input to a parallel output arranging the output to be n bits, e.g., 16 bits in such a way that the first set of 16 bits represents the first pixel in each of the first 16 scan lines the second set of 16 bits represents the second pixel in each of the first 16 scan lines and so on. The serial to binary converter 13 functions the same way for each set of 16 scan lines in each swath that the video camera 11 makes in scanning the surface to be inspected.

The serial to parallel converter 13 is connected to patch generator 14. The patch generator 14 functions to generate patches of 16×16 bits representative of contiguous areas 16×16 pixels each of the test surface. The patch size is arbitrarily chosen to be 16×16 pixels but may, of course, be any size. As previously touched upon and as will be explained further, patch generator 14 generates patches which overlap by fifty percent to insure detection of flaws which occur in adjacent patches. These patches are provided as real time inputs to flaw detector 17.

Memory 15 stores a master, or reference, i.e., a flawless representation of the particular surface to be inspected. In the case of a printed circuit board this would be a stored master or reference of a perfect printed circuit board of the type to be inspected which can be derived from one of many sources such as a printed circuit board determined to be without flaws, art work or photo tool or a digital data base as would exist in a Computer Aided Design (CAD) system.

Memory 15 is connected to a patch generator 16. This patch generator 16 is similar to patch generator 14 in that it provides patches of 16×16 pixels in overlapping configuration of the stored reference to flaw detector 17. The patch generator 16 combines binary numbers representative of 8×8 bit patches to form the binary number representative of 16×16 bit patches. The flaw detector 17 compares each patch of the test surface provided in real time with the corresponding patch of the reference surface from memory 15. On detection of a flaw, the flaw detector 17 may provide an indication and/or a signal by interrupting the control processor.

Figure 2A:
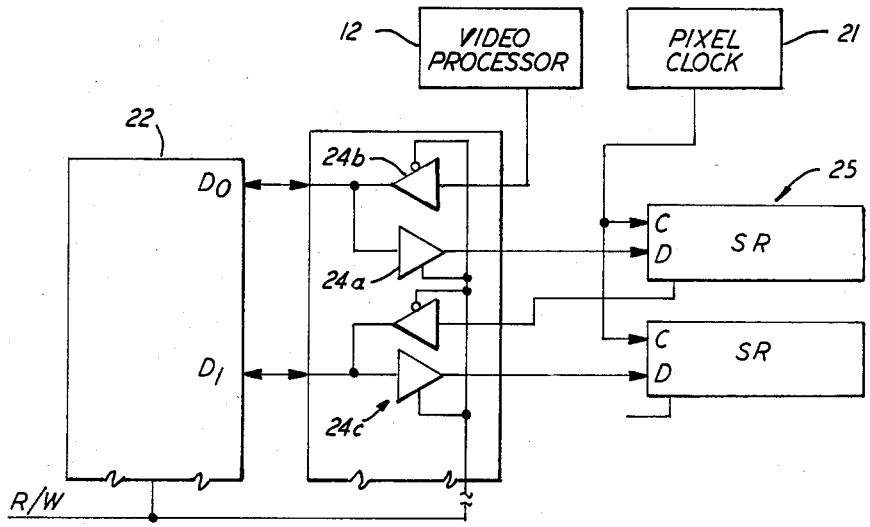
FIG. 2A is a more detailed showing of the transceiver of FIG. 2.
Figure 2:
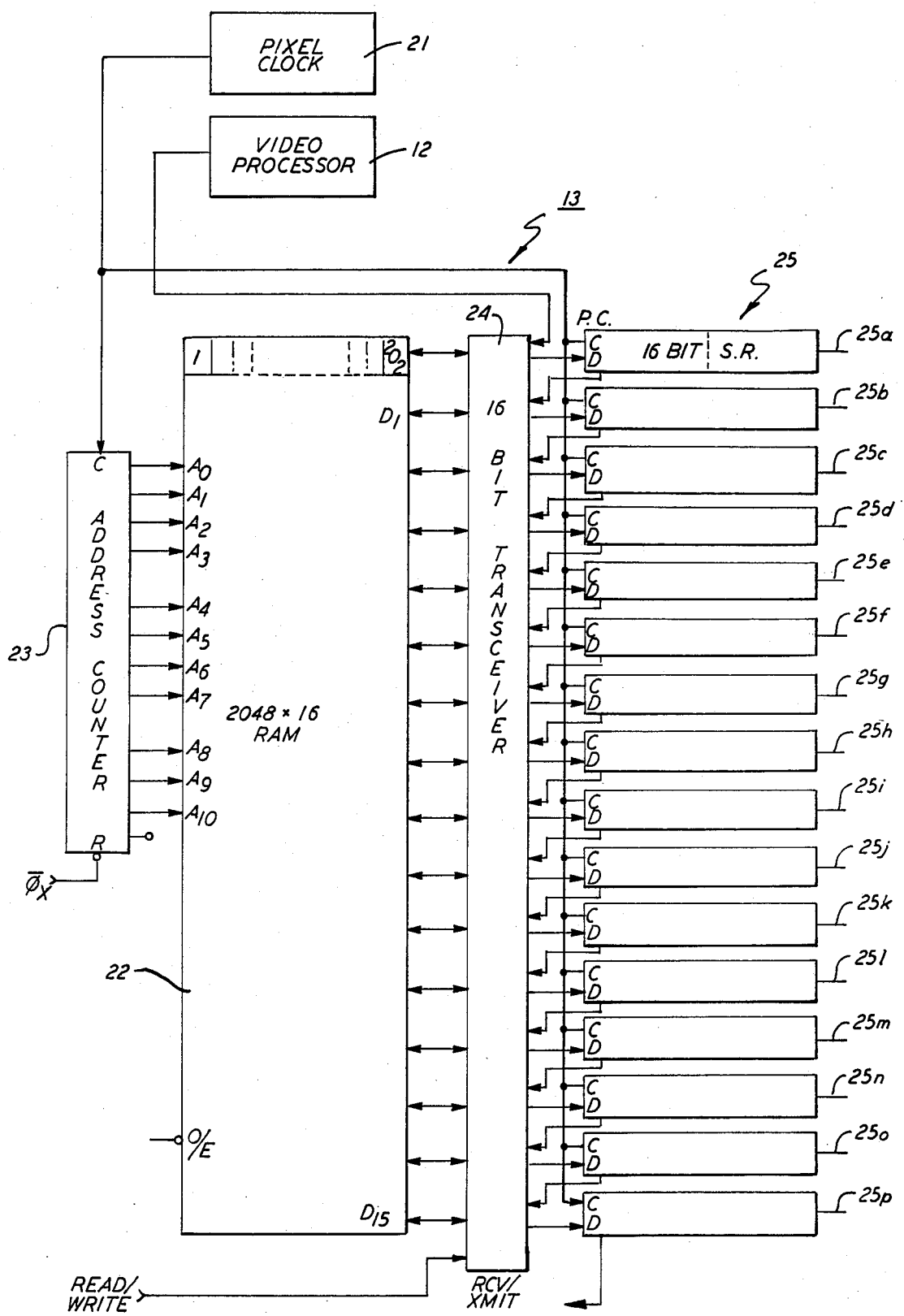
FIG. 2 is a more detailed showing of the serial to parallel converter of FIG. 1.

As seen in FIG. 2, the serial to parallel converter 13 comprises a 2048×16 RAM 22, i.e., the equivalent of sixteen shift registers each capable of storing 2048 bits. Connected to the RAM 22 is an address counter 23 capable of addressing each bit position of the 2048 bit positions in the sixteen registers. For example, the RAM 22 is configured such that the first bit position of the 2048 bit positions are addressed by the address counter 23 in each of the sixteen registers at count 1 and the 2048th bit position of the 2048 bits positions are addressed by the address counter 23 in each of the sixteen registers at count 2048. Thus, at each count of the address counter 23, a sixteen bit word is addressed. At each pixel clock pulse which occur at a 10 MHz rate, the address counter is changed by one. The pixel clock could be any frequency other than 10 MHz and is limited only by the speeds of the devices selected. After the 2048th pixel clock pulse the address counter is reset.

The RAM 22 is connected to a sixteen bit transceiver 24 substantially as shown in FIG. 2. The pixel clock 21 is connected to the address counter 23 and to the clock input of each of the sixteen shift registers 25. Video processor 12 is connected to transceiver 24 and provides video data on a bit by bit basis to RAM 22 as is explained more fully below. A read/write input is also provided to transceiver 24.

The read/write input is derived from the pixel clock 21. The read cycle of the RAM 22 is enabled during the first half of the pixel clock period (when it is "high") at which time the 16 bit word stored from the previous line in read-out from RAM 22 and clocked into each of the 16 shift registers 25. The write cycle of RAM 22 is enabled during the second half of the pixel clock period (when it is "low") at which time the 16 bit word comprised of the current DATA INPUT PIXEL BIT VALUE is written into the $D_o$ input data position of RAM 22 while the first bits of each of the 15 shift registers 25 are written into the $D_1$ thru $D_{15}$ input data positions, respectively, of RAM 22.

In operation the serial to parallel converter 13 functions as follows. On the leading edge of the first pixel clock the address counter 23 is indexed by one and the 16 bit word stored in the first bit position of each of the sixteen 2048 bit registers of RAM 22 is shifted into the first bit position of the virtual sixteen shift registers 25. Before the address changes the first bit of the scan line from video processor 12 is written into the first bit position $D_o$ of the RAM 22. At the same time the bit that was in bit position $D_o$ is written into bit position $D_1$ via the first shift register and what was in bit position $D_1$ is written into bit position $D_2$ via the second shift register etc. down to bit position $D_{15}$, i.e., $D_{14}$ to $D_{15}$ with the bit originally in bit position $D_{15}$ being dumped. This occurs for the entire scan line of 2048 pixels with each successive pixel clock indexing the address counter 23 by one so that the next bit position in each of the virtual sixteen 2048 bit register is addressed. What has happened then on the first pixel clock of the first scan line is that the 16 bit word has changed by one bit with the rest of the bits being shifted down one. On the second pixel clock of the first scan line the same events occur with the difference that it is the 16 bit word in the next bit positions of each of the sixteen registers that is shifted into shift registers 25 and this new word is changed by one bit with the rest of the bits shifted down by one. On the third to two thousand forty-eighth pixel clock of the first scan line the same events occur. On each next scan the process is repeated. If the RAM 22 is originally empty it takes 16 scan lines of one bit pixel data before RAM 22 is filled and a 16 bit word is available at the outputs 25a–25q of the 16 shift registers 25. Thereafter, at each pixel clock the 16 bit word at the outputs of the sixteen shift registers 25 changes. At each pixel clock a new sixteen bit word is presented to patch generator 14 which formulates the 16×16 overlapping bit patches in a manner more fully described below.

The manner in which data is transmitted through, transceiver 24 is shown in FIG. 2A. The transceiver 24 comprises sixteen each of circuits 24a and 24b one set of which is shown in circuit 24c. On the occurrence of a pixel clock the 16 bit pixel word in the addressed bit positions of the sixteen RAM registers is transferred through circuits 24a into shift registers 25 by virtue of a read pulse applied to RAM 22 and the tristate enable input of each circuit 24a. Then the write pulse is applied to the tristate enable of each circuit 24b along with a data bit writes that data bit into the $D_o$ position of the 15 bit word under address. At the same time the bits in the first bit positions of the shift registers 25 are written into the next bit positions of the particular 16 bit work under address, i.e., old $D_o$ goes to $D_1$, old $D_1$ goes to $D_2$ and so on. Block 24c which represents circuits similar to circuits 24a and 24b is shown connected to the first shift register for receiving and transmitting old $D_o$ to $D_1$. While not shown, each of the sixteen shift registers and $D_o$ to $D_{15}$ bit positions have a similar set of circuits 24a and 24b disposed in transceiver 24 for accomplishing the foregoing described transfers between the RAM 22 and sixteen shift registers 25. In further explanation of the transfer when R/W is HIGH circuit 24b is disabled (output goes to high impedance state) and circuit 24a is enabled (output becomes active). When R/W is low circuit 24b is enabled (output goes active) and circuit 24a is disabled. The read/write pulse is essentially the pixel clock pulse.

Figure 3:
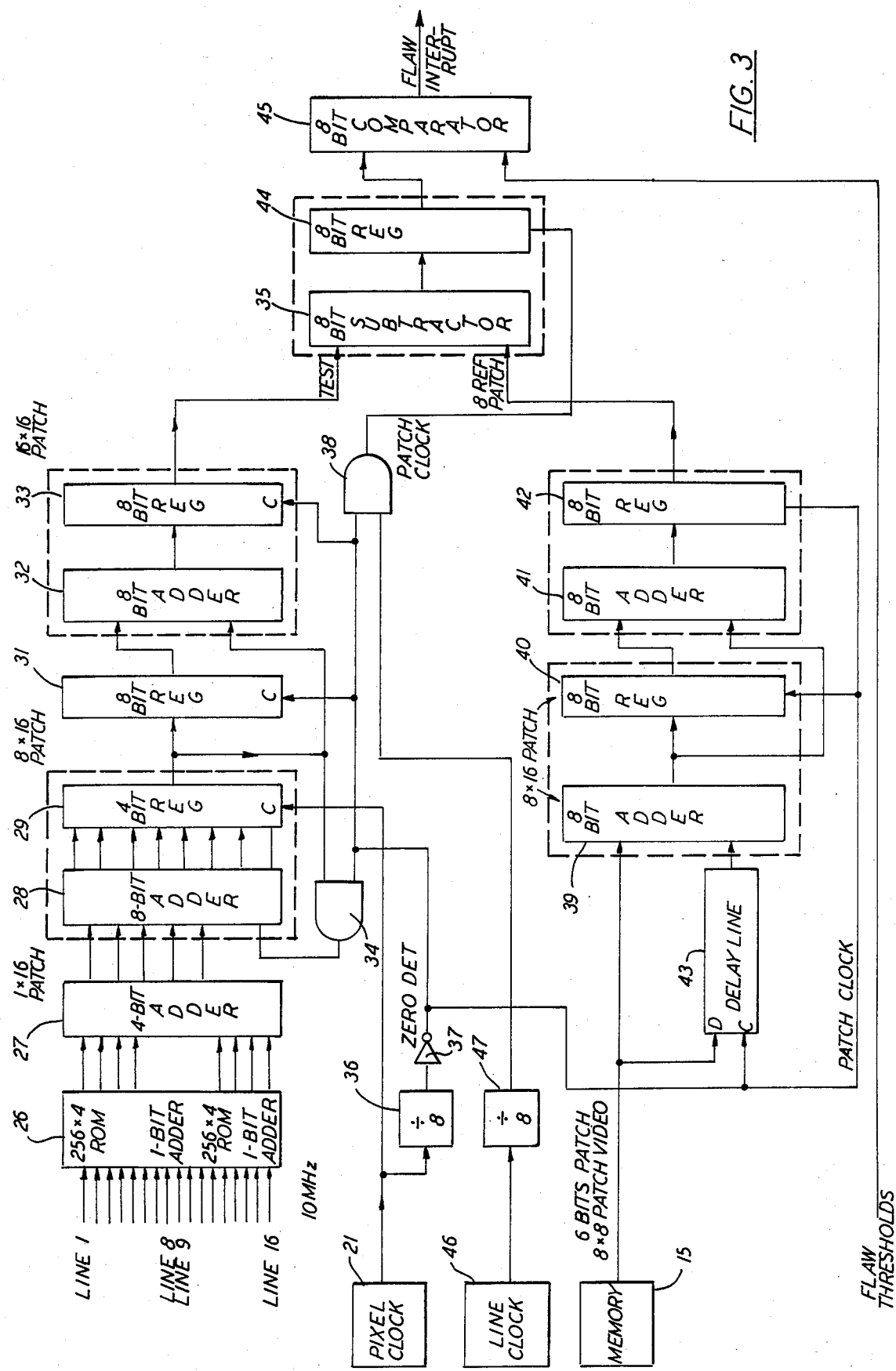
FIG. 3 is a more detailed showing of the patch generators and flaw detector of FIG. 1.

FIG. 3 illustrates the patch generators 14 and 16 and flaw detector 17 in more detail.

The serial to parallel converter 13 provides the sixteen bit word as an input to a pair of one bit adders 26. The pair of one bit adders 26 are connected to four bit adder 27 which is in turn connected to 8 bit adder 28, which in turn is connected to eight bit register 29. The output of eight bit register 29 is connected to the eight bit register 31. In addition, the output of register 29 provides an input to AND gate 34 whose output is connected to eight bit adder 28. The output of eight bit adder 32 is connected to eight bit register 33 whose output is connected to eight bit subtractor 35. The foregoing described structure is essentially the patch generator 14.

The pixel clock 21 is connected directly to the clock input of eight bit register 29 and to divider circuit 36 whose output is connected to zero detector 37. The output of zero detector 37 is connected to the clock inputs of eight bit registers 31 and 33. The output of the zero detector 37 is also connected to one of the inputs of AND circuits 34 and 38.

The patch generator 16 comprises eight bit adder 39, eight bit register 40, eight bit adder 41 and eight bit register 42. Memory 15 is connected to eight bit adder 39 directly and via one line delay 43. The output of eight bit adder 39 is connected to eight bit register 40 and eight bit adder 41 whose output is connected to eight bit register 42. The output of eight bit register 42 is connected to eight bit subtractor 35.

The output of zero detector 37 is connected to the clock inputs of eight bit registers 40 and 42 and the clock input of delay line 43.

The output of eight bit subtractor 35 is connected to eight bit register 44 whose output is connected to eight bit comparator 45. Eight bit comparator 45 has a second input which is representative of the flaw threshold as explained more fully hereinbelow.

The output of AND circuit 38 is connected to the clock input of eight bit register 44 which causes the contents of eight bit register 44 to be transferred to eight bit comparator 45 every eight scan lines. Line clock 46 is connected to divider 47 which provides an input to AND circuit 38 every eight scan lines.

On each pixel clock the sixteen bit word from the shift registers 25 of the serial to parallel converter 13 is provided to one bit adders 26 to provide two four bit words to four bit adder 27. The two four bit words are added in four bit adder 27 whose output is a binary number representative of a $1 \times 16$ patch. This word is then added in eight bit adder 28 to the eight bit output from eight bit register 29. The eight bit word from eight bit register 29 is transferred to the eight bit adder 28 via AND gate 34 on every eighth pixel clock. At the same time each sum from eight bit 29 is clocked in eight bit register 31 so that at the end of eight pixel clocks it is a number representative of an $8 \times 16$ pixel patch. At this time a clock pulse from divider 36 transfers the number stored in eight bit register 31 to the eight bit adder 32 where it is added to the current value from eight bit register 29 to yield numbers representative of overlapping patches of $16 \times 16$ pixels. The effect of the last operation, i.e., delaying the first $8 \times 16$ pixel patch by eight pixel clocks and adding it to the current value produces the fifty percent overlap of the final $16 \times 16$ pixel test patches. The result of the addition in eight bit adder 32 is stored in eight bit register 33 and transferred to eight bit subtractor 35 every eight pixel clocks.

Memory 15 stores $8 \times 8$ pixel patches from which overlapping reference $16 \times 16$ pixel patches are generated. This is accomplished by adding current $8 \times 8$ pixel patches directly from memory to patches which have been delayed by 256 pixel clocks in delay line 43 every eight pixel clocks. In other words, after the data from memory has been initially delayed by 256 pixel clocks, the addition is made in eight bit adder 39 every eight pixel clocks. This delay is necessary since this patch formulation technique is starting with patches which are already in an $8 \times 8$ pixel configuration. The sum from eight bit adder 39 is stored and delayed in an eight bit register 40 and transferred to eight bit adder 41 where it is added to the current value from an eight bit adder 39 and stored in an eight bit register 42. As in the generation of the $16 \times 16$ pixel test patches, the delayed patch is added to the current patch to provide a fifty percent overlapping reference patch of $16 \times 16$ pixels.

Assuming scanning of the video camera or CCD array 11 in the X direction, the foregoing described technique results in overlapping of patches in the x direction. Overlapping patches in the Y direction are obtained every eight pixel clocks via divider 36 and zero detector 37 clocking 8 bit register 33 whose output is overlapping $16 \times 16$ pixel patches every eight pixel clock every line. Register 44 is clocked every eighth line yielding the difference between overlapping $16 \times 16$ pixel test patches every eight pixel and every eight line.

Figure 4:
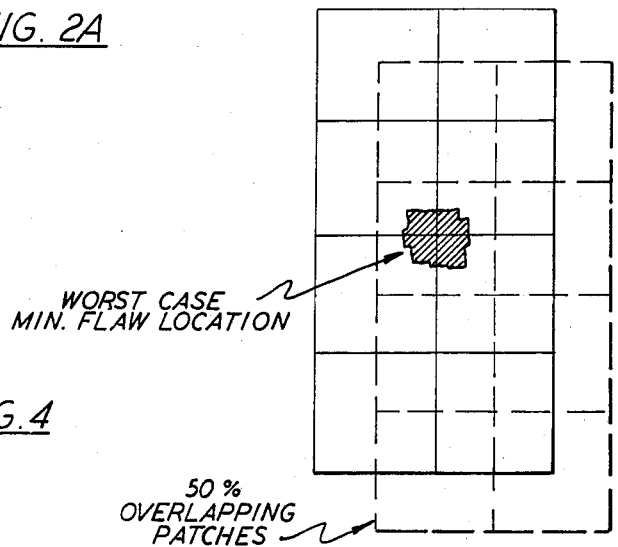
FIG. 4 is a graphical representation of the fifty percent pitch overlap concept of the present invention.

FIGS. 4 illustrates the fifty percent overlapping of patches to insure detection of a flaw that would normally appear in the four adjacent corners of four non-overlapping patches. As shown, the flaw appears completely within a patch when the overlapping technique is used.

At this point it should be noted again that the portions of patches used in generating the $16 \times 16$ test and references pixel patches are binary numbers and the the binary numbers finally appearing at the inputs to eight bit subtractor 35 are eight bit binary numbers. Also, each number represents the sum of reflectances of each pixel in $16 \times 16$ pixel reference and test patches. Thus, when the numbers representative of the total reflectance in each test and reference patch are subtracted, any deviation of a test patch from its corresponding reference patch is given by the difference between the two numbers. This number which changes every eighth pixel clocks or one patch clock is presented to the comparator where it is compared with a number representative of a threshold. When the number from eight bit register 44 exceeds the threshold, a flaw is indicated by a signal from comparator 45 which may be used to interrupt the flaw inspection process.

The threshold is selected to be sufficiently above the noise level. To set the threshold the worst case noise is determined. Since noise is largely due to misregistration of test and reference patches it may be computed as follows:

$$\text{Noise} = 2n\, Em - Em^2 \text{ in pixel units}$$

where:
n = number of pixels per side of a patch
Em = worst case misregistration in pixels
when n = 16 pixels
Em = 1.5 pixels
Noise = 45.75 pixels Therefore, the flaw threshold must be set above 45.75 pixels, i.e., above 18% of patch area in order to detect flaws with a high degree of certainty. This limits the maximum detectable flaw to 45.75 pixels which is equivalent to a square of about 7 pixels per side. The threshold may, of course, be varied, up or down depending on the worst case of misregistration of the system.

For purposes of this invention it may be assumed that there is perfect registration between test patches provided in real time by the video scan of the test surface and the reference patches provided by memory so that each test patch is compared to its corresponding reference patch. However, in actual practice, registration between test and reference patches is desirable. Any registration which enables the determination of a flaw threshold may be used. However, the one preferred for the present, detector is disclosed in U.S. Ser. No. 745,968 filed June 17, 1985 entitled "Misregistration/Distortion Correction Scheme" filed concurrently with and having the same Assignee as the present application now U.S. Pat. No. 4,668,982, issued May 26, 1987.

Other modifications of the present invention are possible in light of the above described invention which should not be deemed as placing limitations on the invention other than those expressly set forth in the claims which follow:

What is claimed is:

1. In a system for processing image data on a surface;
   scanning means for scanning the surface across its length at a plurality of arbitrarily selected scan lines each one of which comprises a plurality of picture elements;
   said scanning means providing as an output a serial stream of bits for each of said scan lines each bit representative of one of said picture elements in a scan line;
   means for formulating said serial streams of bits into binary numbers each representative of the reflectance value of a patch of contiguous picture elements composed of n×n picture elements each.

2. In a system according to claim 1 wherein said means for formulating comprises:
   first means for rearranging said stream of bits into words of n bits such that the first word comprises the first bit of each group of n scan lines with each successive word comprising the next bit of each group of n scan lines and providing each word of n bits as an output equivalent to a patch of 1×n bits.

3. In a system according to claim 2 wherein said means for formulating comprises:
   second means connected to said first means for adding each word of n bits to form patches equivalent to n×n picture elements.

4. In a system according to claim 1 wherein said first means comprises:
   memory means comprising n storage registers each capable of storing all the bits in a scan line;
   address means connected to said memory means for addressing successively the first through last bit positions in each of said storage registers such that a word of n bits is addressed at each bit position of said storage registers;
   shift register means comprising n shift registers, each having n bit positions;
   transceiver means connected to said scanning means and between said memory means and said shift register means for shifting the bits in each addressed bit position of said shift registers into respective ones of said shift registers, writing each bit so shifted back into said addressed bit position of each of said storage registers but down by one significant bit position, and inserting the next available bit from said scanning means into the least significant bit position of each addressed bit position of said storage registers whereby when said shift registers are filled said shift register means provides a new n bit word as in an output every time the address changes.

5. In a system according to claim 3 wherein said first means comprises:
   memory means comprising n storage registers each capable of storing all the bits in a scan line;
   address means connected to said memory means for addressing successively the first through last bit positions in each of said storage registers such that a word of n bits is addressed at each bit position of said storage registers;
   shift register means comprising n shift registers, each having n bit positions;
   transceiver means connected to said scanning means and between said memory means and said shift register means for shifting the bits in each addressed bit position of said shift registers into respective ones of said shift registers, writing each bit so shifted back into said addressed bit position of each of said storage registers but down by one significant bit position, and inserting the next available bit from said scanning means into the least significant bit position of each addressed bit position of said storage registers whereby when said shift registers are filled said shift register means provides a new n bit word as in a output every time the address changes.

6. In a system according to claim 1 wherein said means for formulating comprises:
   pixel clock means providing clock pulses at a predetermined rate;
   memory means comprising a plurality of storage registers each of said storage registers capable of storing all the bits in a scan line;
   a like plurality shift register;
   transceiver means connected between said shift registers and said memory means for shifting the bits at a selected bit position in each of said storage registers to respective ones of said shift registers, writing each bit so shifted back into said selected bit position of each of said storage registers but down by one significant bit position.

7. A system for detecting flaws on a test surface comprising:

scanning means for scanning the surface across its length at a plurality of scan lines each one of which comprises a plurality of picture elements;

said scanning means providing as an output a serial stream of bits for each of said scan lines each bit representative of one of said picture elements in a scan line;

first means connected to said scanning means for formulating said serial streams of bits into binary numbers each representative of a reflectance value of a patch of said test surface composed of contiguous n×n picture elements;

memory means storing an image of a referenc surface;

second means connected to said memory means for formulating said stored image into binary numbers each representative of a patch of said reference surface composed of contiguous n×n picture elements;

means for comparing said binary numbers of corresponding test and reference surfaces for determining whether said test surface contains a flaw.

8. A system according to claim 7 wherein said first and second means each include:

delay means providing overlapping of said patches representative of said test surface and overlapping of said patches representative of said reference surface.

9. A system according to claim 7 wherein said first means, comprises:

third means connected to said scanning means for formulating said serial stream of bits into parallel outputs each representative of a word n bits in length with the first word consisting of the first bit in each of n scan lines and each successive word consisting of the next bit in each of said n scan lines repetitively for each group of n scan lines scanned.

10. A system according to claim 8 wherein said first means, comprises:

third means connected to said scanning means for formulating said serial stream of bits into parallel outputs each representative of a word n bits in length with the first word consisting of the first bit in each of n scan lines and each successive word consisting of the next bit in each of said n scan lines repetitively for each group of n scan lines scanned.

11. A system according to claim 10 wherein said first means further comprises:

fourth means connected to said third means for adding each group of n consecutive words of n bits from said third means to provide binary number outputs each representative of a n×n patch of contiguous n×n picture elements of said test surface.

12. A system according to claim 11 wherein said memory means stores patches equal to n/2×n/2 picture elements;

fifth means connected to said memory means for adding patches from said memory to provide patches of n×n picture elements.

13. A system according to claim 12 further including:

subtractor means connected to said fourth and fifth means providing an output equal to the difference between the numbers representative of corresponding patches;

comparator means connected to said subtractor means;

means providing a threshold to said comparator means whereby said comparator means provides a signal whenever the output from said subtractor means exceeds said threshold.

* * * * *